United States Patent [19]
Schnurr et al.

[11] Patent Number: 5,874,607
[45] Date of Patent: Feb. 23, 1999

[54] COPRODUCTION OF 6-AMINOCAPRONITRILE AND HEXAMETHYLENEDIAMINE

[75] Inventors: Werner Schnurr, Herxheim; Guido Voit, Schriesheim; Klemens Flick, Herxheim; Rolf-Hartmuth Fischer, Heidelberg, all of Germany

[73] Assignee: BASF Aktiengesellschaft, Ludwigshafen, Germany

[21] Appl. No.: 635,653

[22] Filed: Apr. 22, 1996

[30] Foreign Application Priority Data

Apr. 11, 1996 [DE] Germany .................. 196 14 283.0

[51] Int. Cl.$^6$ .................................................. C07C 255/03
[52] U.S. Cl. ............................................................ 558/459
[58] Field of Search ............................................... 558/459

[56] References Cited

U.S. PATENT DOCUMENTS 5,557,004  9/1996  Flick et al. .............................. 558/459

*Primary Examiner*—Joseph McKane
*Attorney, Agent, or Firm*—Keil & Weinkauf

[57] ABSTRACT

A process for the coproduction of 6-aminocapronitrile (ACN) and hexamethylenediamine (HMD) by treatment of adiponitrile (ADN) with hydrogen in the presence of a nickel-containing catalyst at temperatures not below room temperature and elevated hydrogen partial pressure in the presence or absence of a solvent comprises, after the conversion based on ADN and/or the selectivity based on ACN has or have dropped below a defined value (a) interrupting the treatment of ADN with hydrogen by stopping the feed of ADN and of the solvent, if used, (b) treating the catalyst at from 150° to 400° C. with hydrogen using a hydrogen pressure within the range from 0.1 to 30 MPa and a treatment time within the range from 2 to 48 h, and (c) then continuing the hydrogenation of ADN with the treated catalyst of stage (b).

8 Claims, No Drawings

COPRODUCTION OF 6-AMINOCAPRONITRILE AND HEXAMETHYLENEDIAMINE

The present invention relates to an improved process for the co-production of 6-aminocapronitrile (ACN) and hexamethylenediamine (HMD) by treatment of adiponitrile (ADN) with hydrogen in the presence of a nickel-containing catalyst at temperatures not below room temperature and elevated hydrogen partial pressure in the presence or absence of a solvent.

The present invention further relates to a process wherein the treatment of ADN is carried out in suspension or in a fixed bed in a downflow or outflow process.

The hydrogenation of ADN to 6-aminocapronitrile in the presence of solvents, especially ammonia, and nickel-containing catalysts has been described in detail for example in US-A 2,762,835, US 2,208,598 and WO 92/21650.

The nickel-containing catalysts used in the hydrogenation of ADN lose activity in long runs and therefore have to be replaced with new catalysts once the activity has dropped below a certain value.

Nickel-containing catalysts are widely used in industry for steam reforming, for methanization and for the hydrogenation of functional groups such as CO double bonds, C—C multiple bonds or nitrile groups. In many of the aforementioned applications the catalyst is deactivated sooner or later through the formation of carbonaceous deposits on the active catalyst surface. The formation of carbonaceous deposits in steam reforming and the removal of these layers by reaction with oxygen, hydrogen, steam or carbon dioxide is described in Trimm, Catal. Rev.Sci. Eng., 16(2), 155–187 (1977). Measurable reaction rates are achieved with hydrogen only at temperatures above 550° C.

The regeneration of catalysts coated with carbonaceous deposits is generally effected by burning off the organic coatings with nitrogen-air mixtures. However, this method can be used only with catalysts which remain stable on reaction with air supported catalysts with a stable structure of oxidic material, such as $SiO_2Al_2O_3$, $TiO_2$, can be successfully regenerated by this method. For instance, GB-A 2,284,163 describes the regeneration of a supported catalyst with Pt, Pd, Ru, Rh, etc. or nickel by treatment of a gas containing at least chlorine and oxygen.

Catalysts with very high metal contents become damaged on burning off the organic deposits with air, altering their mechanical properties (see EP-A 61,042).

EP-A 61,042 also discloses that nickel-containing catalysts having a maximum nickel content of 50% by weight for the hydrogenation of butynediol to butanediol can be regenerated by hydrogen treatment at temperatures between 200 and 500° C., preferably at temperatures above 275° C.

Similarly, US-A 5,310,713 describes a regeneration with hydrogen for an alkylation catalyst which may contain nickel, but the regeneration with hydrogen is carried out in the presence of liquid alkane and of a chloride source.

It is known from Journal of Catalysis 143 (1993), 187–200, that a nickel catalyst (25% by weight of Ni on $SiO_2$) which is used for the hydrogenation of acetonitrile in the gas phase can be regenerated by treatment with hydrogen at temperatures of above 200° C.

The cited references do not reveal whether it is also possible to regenerate nickel-containing catalysts used in the hydrogenation of higher boiling dinitriles, especially adiponitrile. For bifunctional compounds such as dinitriles, in particular, can give rise, under reaction conditions, to the formation of oligomers which lead to regeneration problems.

It is an object of the present invention to provide a process whereby it is possible to regenerate the nickel-containing catalysts used in hydrogenation of ADN to ACN and HMD in a simple way, without incurring long shutdown times during the regeneration of the catalysts. More particularly, the object is to raise catalyst activity in respect of conversion and selectivity in the hydrogenation of ADN as closely as possible to the level of the unused catalyst.

We have found that these objects are achieved by a process for the coproduction of 6-aminocapronitrile (ACN) and hexamethylenediamine (HMD) by treatment of adiponitrile (ADN) with hydrogen in the presence of a nickel-containing catalyst at temperatures not below room temperature and elevated hydrogen partial pressure in the presence or absence of a solvent, which comprises, after the conversion based on ADN and/or the selectivity based on ACN has or have dropped below a defined value (a) interrupting the treatment of ADN with hydrogen by stopping the feed of ADN and of the solvent, if used, (b) treating the catalyst at from 150 to 400° C. with hydrogen using a hydrogen pressure within the range from 0.1 to 30 MPa and a treatment time within the range from 2 to 48 h, and (c) then continuing the hydrogenation of ADN with the treated catalyst of stage (b).

The nickel catalysts used can be customary Raney nickel catalysts (as fixed-bed or suspension catalysts) or supported catalysts. Raney nickel catalysts are known and commercially available or preparable in a known manner from a nickel-aluminum alloy by treatment with a base such as sodium hydroxide solution. The support used may typically be alumina, silica, activated carbons, titania and zirconia. Supported catalysts customarily have a nickel content within the range from 3 to 95, preferably 20 to 95, especially from 50 to 95,% by weight, based on the total mass of nickel and support.

The catalysts may also be modified, if desired, with metals of group VIB (Cr, Mo, W) and VIII of the periodic table (Fe, Ru, Os, Co, Rh, Ir, Pd, Pt) and also with copper, rhenium or manganese, in which case the nickel content of the catalyst is generally within the range from 50 to 99.9, preferably from 80 to 99,% by weight, based on the active components (nickel+modifier).

Furthermore, the catalysts may be modified with a compound based on an alkali metal or an alkaline earth metal such as lithium, sodium, potassium, rubidium, cesium, magnesium, calcium, strontium and barium, especially cesium. It is customary to use a weight ratio within the range from 0 to 5, preferably from 0.1 to 3,% by weight of alkali metal or alkaline earth metal to nickel.

The nickel catalysts usable according to the invention may be prepared in various ways. The preparation of supported nickel catalysts is customarily effected by impregnating a ceramic support with an aqueous organic solution of a nickel salt and, if desired, the modifier, then drying and calcining in a conventional manner. The solubility of the salts and pore volume of the support limits, according to observations to date, the amount of nickel which can be applied by one impregnating step, so that, if desired, the impregnating procedure may have to be repeated more than once, in which case, in general, the catalyst is dried and calcined after each impregnating step in order that the desired level of nickel may be obtained on the catalyst. It is also possible to apply nickel by precipitation of a sparingly soluble nickel compound such as the corresponding hydroxide or carbonate compound to a support suspended in the precipitation solution. The precipitates can be shaped in a conventional manner, customarily after filtration or spray drying.

The hydrogenations can be carried out with preference in upflow, downflow or suspension processes.

When the reaction is carried out in a suspension, it is customary to choose temperatures within the range from 40 to 150° C., preferably within the range from 50 to 100° C., particularly preferably within the range from 60 to 90° C.; the pressure is generally chosen to be within the range from 2 to 20, preferably 3 to 10, particularly preferably from 4 to 9, MPa. The residence times are essentially dependent on the desired yield, selectivity and the desired conversion; customarily, the residence time is selected so as to maximize the yield, for example within the range from 50 to preferably within the range from 70 to 200, min.

In the suspension process, the solvent used is preferably ammonia, amines, diamines and triamines having from 1 to 6 carbon atoms such as trimethylamine, triethylamine, tripropylamine and tributylamine or alcohols, especially methanol and ethanol, particularly preferably ammonia. It is advantageous to use a dinitrile concentration within the range from 10 to 90, preferably from 30 to 80, particularly preferably from 40 to 70,% by weight, based on the sum of dinitrile and solvent.

The amount of catalyst used is generally within the range from 1 to 50, preferably from 5 to 20,% by weight, based on the amount of dinitrile used.

The suspension hydrogenation can be carried out batchwise or, preferably, continuously, generally in the liquid phase.

The hydrogenation may also be carried out batchwise or continuously in a downflow or upflow process in a fixed-bed reactor, in which case it is customary to employ a temperature within the range from 20 to 150° C., preferably within the range from 30 to 90° C., and a pressure generally within the range from 2 to 30, preferably within the range from 3 to 20, MPa. The hydrogenation is preferably carried out in the presence of a solvent, preferably ammonia, amines, diamines and triamines having from 1 to 6 carbon atoms such as trimethylamine, triethylamine, tripropylamine and tributylamine or alcohol, preferably methanol and ethanol, particularly preferably ammonia. In a preferred embodiment, the amount of ammonia used is within the range from 0.5 to 10, preferably from 1 to 6, g per g of adiponitrile. Preference is given to using a catalyst space velocity within the range from 0.1 to 2.0, preferably from 0.3 to 1.0, kg of adiponitrile/l*h. Here too it is possible to adjust the conversion and hence the selectivity in a specific manner by varying the residence time.

The hydrogenation can be carried out in a customary suitable reactor.

If the reaction is carried out in the gas phase, it is customary to use temperatures within the range from 100° to 250° C., preferably within the range from 160° to 200° C.; the pressure employed is generally within the range from 0.01 to 3, preferably from 0.09 to 0.5, MPa. Furthermore, the molar ratio of hydrogen to ADN is generally within the range from 2:1 to 300:1, preferably within the range from 10:1 to 200:1.

In a preferred embodiment, the hydrogenation of ADN is carried out in the presence of ammonia as solvent using fixed-bed catalysts as described above by a process wherein, following the deactivation of the catalyst, ie. a decrease in the conversion of ADN and/or selectivity based on ACN below a defined value, first the feed of adiponitrile and ammonia is switched off, then the temperature is brought to 200°–250° C., and subsequently the catalyst is treated for from five to six hours with from 200 to 800, preferably from 500 to 700, especially 600, l of hydrogen/l of cat.×h. Thereafter the temperature is customarily brought back down to reaction temperature and the hydrogenation is continued.

Prior to starting the regeneration, it is preferable to remove the hydrogenation mixture still present in the reactor. It may further be advantageous, especially if the treatment of the ADN with hydrogen is carried out in suspension, to wash the catalyst before the actual regeneration, ie. after interruption of the treatment of ADN with hydrogen (stage (a)) and before treatment with hydrogen (stage (b)), with the solvent present in the system, especially with liquid ammonia. The wash temperature employed is customarily within the range from 20° to 200° C., especially within the range from 20° to 100° C. It is generally advantageous to carry on the wash for a period of from 2 to 24 hours.

From experience to date, the regeneration can be carried out at any desired time. From an economic point of view, a regeneration appears to be sensible when the conversion based on ADN and/or the selectivity based on ACN has dropped by more than 10%, based on the initial value.

According to the invention, the regeneration of the catalyst is carried out at temperatures within the range from 150° to 400° C., preferably within the range from 180° to 270° C., especially within the range from 200° to 250° C., using a hydrogen pressure within the range from 0.1 to 30 MPa, preferably within the range from 0.1 to 20 MPa, and a treatment time within the range from 2 to 48 h, preferably within the range from 2 to 24 h. A continuous process is customarily carried out with the hydrogen rate within the range from 100 to 1500, preferably within the range from 200 to 1000, l of hydrogen/l of reactor volume×hour.

The process of the invention makes it possible to achieve distinct improvements in the life and space-time yield of nickel catalysts in the hydrogenation of adiponitrile to 6-aminocapronitrile and hexamethylenediamine (nylon 6 and nylon 66 intermediates).

EXAMPLES

Example 1 (suspension hydrogenation)

Reactor: 250 ml autoclave with sampling port (material of construction: HC 4); agitation by disk stirrer.

Batch: in each case 48 g of ADN, 5.6 g of Raney nickel (BASF, H 1-50, water-moist).

Raney nickel was introduced into an autoclave under a protective gas (argon). The autoclave was then sealed and 150 ml of liquid $NH_3$ were injected. After brief stirring, the bulk of the ammonia was pressed out of the reactor via a riser pipe equipped with a frit. This process was repeated six times with 50 ml of liquid ammonia each time to obtain anhydrous Raney nickel as a representative starter catalyst (ammonia holdup about 100 ml). Thereafter the system was heated to 80° C., 48 g of adiponitrile were metered in, and the pressure was raised with hydrogen to 7 MPa. Catalyst-free samples of the liquid phase were removed through the sampling port after 20, 45, 90, 135, 180 and 225 min.

After 225 min, the temperature in the reactor was reduced to 25° C. and the catalyst-free reaction mixture was removed. The catalyst remaining in the reactor was rinsed six times with 50 ml of liquid ammonia each time, at room temperature, by the method described for the wash prior to the first use. For the subsequent run the system was heated back up to 80° C. and the reactants were metered in afresh. The runs with sampling and washing were repeated a number of times.

Table 1 shows the conversion of the adiponitrile and the selectivity to 6-aminocapronitrile as evident from the GC data after a hydrogenation time of 225 min. Apart from ACN, hexamethylenediamine was formed almost exclusively.

TABLE 1

| Run | ADN conversion | ACN selectivity |
|---|---|---|
| 1 | 84.2 | 59.6 |
| 2 | 49.6 | 70.4 |
| 3 | 43.4 | 64.7 |
| 4 | 37.3 | 70.1 |
| 5 | 30.6 | 75.2 |
| 6 | 29.2 | 75.2 |
| 7 | 26.3 | 77.2 |
| 8 | 24.2 | 80.0 |
| 9 | 17.3 | 79.5 |
| 10 | 16.2 | 85.0 |
| 11 | 13.2 | 81.6 |
| 12 | 9.0 | 86.8 |
| 13 | 7.4 | 95.3 |
| 14 | 6.0 | 85.5 |
| 15 | 5.3 | 84.6 |
| 16 | 5.4 | 87.2 |
| 17 | 4.9 | 90.3 |
| 18 | 5.8 | 88.2 |

Following run 18, the hydrogenation mixture was removed and the deactivated catalyst was rinsed six times with liquid ammonia. Thereafter the ammonia was completely decompressed and entirely displaced from the reactor using argon. The reactor was then heated to 100° C. and once more flushed with argon. The argon was then displaced by flushing with hydrogen. The reactor was then heated to 250° C. and the pressure set with hydrogen to 10 MPa. The reactor was left at 250° C. for 5 hours. The autoclave was then cooled down to room temperature, the gas phase was completely decompressed, and the next block of runs was started.

TABLE 2

| Run after regeneration of catalyst | | |
|---|---|---|
| Run | ADN conversion | ACN selectivity |
| 19 | 54.9 | 80.5 |

Regeneration with hydrogen made it possible to raise the conversion based on ADN from 5.8% to 54.9%.

Example 2 (continuous gas phase hydrogenation)
Catalyst preparation: 4 mm $Al_2O_3$ extrudates (SPH 512 B, Rhône Poulenc) were initially impregnated for two hours at room temperature with an aqueous, 3.5% strength by weight $CsNO_3$ solution, then air-dried at 120° C. for 16 h and subsequently calcined in air at 350° C. over 4 h. The extrudates thus calcined were then impregnated with an aqueous, 44.3% strength by weight $Ni(No_3)_2$ solution for 2 h, then air-dried at 120 ° C. for 16 h and subsequently calcined in air at 350° C. over 4 h. Thereafter the impregnation, drying and calcining was repeated with the nickel salt solution.

After cooling, the extrudates were installed in a reduction apparatus and flushed for 2 h at room temperature with 20 l/h of $N_2$ to remove air. This was followed by heating to 300° C. with a heating rate of 2° C./min and a hydrogen flow of 20 l/h of $H_2$ and the 300° C. were maintained for 2 h.

The catalyst thus prepared contained 0.1% by weight of Cs and 13% by weight of Ni, based on the total weight of the extrudates.

Hydrogenation:
40 g/h of adiponitrile were introduced into a vaporizer (280° C.) and passed from there with 400 l/h of hydrogen through a tubular reactor (packed with 330 g of catalyst; reactor dimensions: length=2000 mm, diameter=15 mm) in the downflow direction. The reactor temperature was 180° C. The gaseous reactor effluent was condensed in cold traps and analyzed by gas chromatography. Following a startup phase, the adiponitrile conversion obtained was 45.2%, which dropped to 24.1% over a period of 445 h. The aminocapronitrile selectivity was within the range from 80 to 90%. The dinitrile feed was then turned off and the catalyst regenerated in the reactor with 200 l/h of hydrogen at 250° C. over 6 hours. Following renewed startup under identical conditions (see above), a conversion of 42.7% was obtained; that is, the catalyst had almost been restored to its initial activity.

Example 3 (fixed-bed hydrogenation in the liquid phase):

Catalyst preparation 2.5 kg of an NiAl alloy (from BASF, H1-55) were impregnated at 80° C. with stearic acid. After comminution of the cooled and solidified mass, the powder obtained was pressed into tablets (3 height, 3 mm diameter). The tablets thus obtained were then calcined at 900° C. over 2 h. The activation of the tablets was carried out with sodium hydroxide solution. For this, 2.4 kg of the tablets were introduced into 5.7 l of water and then admixed with vigorous stirring to a total of 1.44 kg of NaOH platelets. On completion of the addition the stirring was continued at 90° C. for further 24 h. After cooling, the activated tablets were washed with water until the wash liquor was pH-neutral.

The activated catalyst tablets were installed in the reactor under water and rinsed with ammonia.

Hydrogenation: 370 g/h of adiponitrile and 1.1 kg/h of ammonia were passed with 500 l/h of hydrogen through a tubular reactor (packed with 740 ml of catalyst; length=1800 mm, diameter 30 mm) in the upflow direction. The reactor temperature was 50° C., the pressure was 20 MPa. The reactor effluent was analyzed by gas chromatography. Following a startup phase an adiponitrile conversion of 45% was obtained, which dropped to 20% over a period of 280 hours. The aminocapronitrile selectivity rose from initially 80 to 90%.

The dinitrile and ammonia feed were then switched off and the catalyst regenerated in the reactor at 200° C. and a hydrogen pressure of 20 MPa (at 500 l/h of hydrogen) for 5 hours newed startup under identical conditions (see above) the conversion rose to 45% (at an ACN selectivity of 80%); that is, the catalyst had been restored to its initial activity.

We claim:
1. A process for preparing an $NH_2$-containing compound by hydrogenating a compound having at least one unsaturated carbon-nitrogen bond with hydrogen in the presence of a catalyst at an elevated hydrogen partial pressure in the presence or absence of a solvent, which comprises
   a) using a catalyst comprising a cobalt- and/or iron catalyst, and
   b) interrupting the hydrogenation by stopping the feed of the compound to be hydrogenated,
   (c) treating the catalyst at from 150° to 400° C. with hydrogen using a hydrogen pressure within the range from 0.1 to 30 MPa and a treatment time within the range from 2 to 48h, and subsequently continuing the hydrogenation of the compound having at least one unsaturated carbon-nitrogen bond.

2. The process of claim 1, wherein the compound having at least one unsaturated carbon-nitrogen bond is a $C_4$–$C_8$- alkylnitrile, a $C_5$–$C_8$-cycloalkylnitrile, a $C_4$–$C_8$-alkyldinitrile or a $C_5$–$C_8$-cycloalkyldinitrile.

3. The process of claim 1, wherein the compound having at least one unsaturated carbon-nitrogen bond is adiponitrile and 6-aminocapronitrile and hexamethylenediamine are obtained in the process.

4. The process of claim 1, wherein the hydrogenation of the compound having at least one unsaturated carbon-nitrogen bond is carried out in suspension at a temperature within the range from 40° to 150° C. and at a pressure within the range from 2 to 20 MPa.

5. A process as claimed in any of claims 1 to 3, wherein the hydrogenation of the compound having at least one unsaturated carbon-nitrogen bond is carried out in a fixed-bed reactor in a downflow or upflow process at a temperature within the range from 30° to 200° C. and at a pressure within the range from 2 to 30 MPa.

6. A process for regenerating a cobalt- and/or iron catalyst, which comprises treating the catalyst with hydrogen at from 150 to 400° C. using a hydrogen pressure within the range from 0.1 to 30 MPa and a treatment time within the range from 2 to 48 h.

7. The process of claim 3, wherein the hydrogenation of adiponitrile is carried out in suspension at a temperature within the range of from 40° to 150° C. and at a pressure within the range of 2 to 20 MPa.

8. The process of claim 3, wherein the hydrogenation of adiponitrile is carried out in a fixed-bed reactor in a downflow or upflow process at a temperture within the range from 30 to 200° C. and at a pressure within the range from 3 to 30 MPa.

* * * * *

UNITED STATES PATENT AND TRADEMARK OFFICE
CERTIFICATE OF CORRECTION

PATENT NO. : 5,874,607
DATED : February 23, 1999
INVENTOR(S) : Schnurr et al.

Page 1 of 6

It is certified that error appears in the above-identified patent and that said Letters Patent is hereby corrected as shown below:

The title page should be deleted to appear as per attached title page.

Please delete columns 1-8 and substitute columns 1-8 as per attached.

Signed and Sealed this

Fourth Day of December, 2001

Attest:

*Nicholas P. Godici*

Attesting Officer

NICHOLAS P. GODICI
Acting Director of the United States Patent and Trademark Office

United States Patent [19]

Schnurr et al.

[11] Patent Number: 5,874,607
[45] Date of Patent: Feb. 23, 1999

[54] COPRODUCTION OF 6-AMINOCAPRONITRILE AND HEXAMETHYLENEDIAMINE

[75] Inventors: Werner Schnurr, Herxheim; Guido Voit, Schriesheim; Klemens Flick, Herxheim; Rolf-Hartmuth Fischer, Heidelberg, all of Germany

[73] Assignee: BASF Aktiengesellschaft, Ludwigshafen, Germany

[21] Appl. No.: 08/635,653

[22] Filed: Apr. 22, 1996

[30] Foreign Application Priority Data

Apr. 11, 1996 [DE] Germany ............ 196 142 83

[51] Int. Cl.[6] ............... C07C 255/03
[52] U.S. Cl. .................. 558/459
[58] Field of Search .................. 558/459

[56] References Cited

U.S. PATENT DOCUMENTS 5,557,004   9/1996   Flick et al. ................ 558/459

Primary Examiner—Joseph McKane
Attorney, Agent, or Firm—Keil & Weinkauf

[57] ABSTRACT

A process for preparing an $NH_2$-containing compound by hydrogenating a compound containing at least one unsaturated carbon-nitrogen bond with hydrogen in the presence of a catalyst at temperatures not below room temperature and elevated hydrogen partial pressure in the presence or absence of a solvent which comprises a) using a catalyst comprising a cobalt- and/or iron-containing catalyst, and b) after the conversion based on the compound to be hydrogenated and/or the selectivity based on the desired product has or have dropped below a defined value or the amount of an unwanted by-product has risen beyond a defined value, interrupting the hydrogenation by stopping the feed of the compound to be hydrogenated and of the solvent, if used, c) treating the catalyst at from 150 to 400° C. with hydrogen using a hydrogen pressure within the range from 0.1 to 30 MPa and a treatment time within the range from 2 to 48 h, and d) subsequently continuing the hydrogenation of the compound containing at least one unsaturated carbon-nitrogen bond.

8 Claims, No Drawings

COPRODUCTION OF 6-AMINOCAPRONITRILE AND HEXAMETHYLENEDIAMINE

The present invention relates to an improved process for preparing an $NH_2$-containing compound by hydrogenating a compound containing at least one unsaturated carbon-nitrogen bond with hydrogen in the presence of a catalyst at temperatures not below room temperature and elevated hydrogen partial pressure in the presence or absence of a solvent.

The present invention further relates to a process for preparing specifically 6-aminocapronitrile (ACN) and hexamethylenediamine (HMD), a process wherein the hydrogenation of compounds containing at least one unsaturated carbon-nitrogen bond is carried out in suspension or in a fixed-bed reactor in a downflow or upflow process, and a process for regenerating cobalt- and/or iron-containing catalysts.

The hydrogenation of unsaturated carbon-nitrogen bonds with hydrogen is described for example in Houben-Weyl, Vol. 11/1 (nitrogen compounds II, amines), pages 545–574, 4th edition, 1957.

U.S. Pat. No. 2,257,814 discloses a process for preparing aminonitriles from dinitriles by conducting the hydrogenation in the liquid phase in the presence of cobalt- and optionally iron-containing catalysts. Furthermore, DE-A 848,654 describes the partial hydrogenation of adiponitrile (ADN) to ACN in the presence of fixed-bed catalysts based on copper/cobalt/zinc and iron-cobalt spinels. DE-A 954,416 describes the use of cobalt on silica gel as a catalyst for preparing aminonitriles and diamines by hydrogenation of dinitriles with hydrogen. DE-A 4,235,466 describes a process for preparing cycloaliphatic and aliphatic aminonitriles by catalytic hydrogenation in the presence of a catalyst prepared from iron sponge.

The cobalt- and iron-containing catalysts used in the hydrogenation of nitriles and imines lose activity in long runs and therefore have to be replaced with new catalysts once certain limits have been reached in respect of conversion and/or selectivity or by-product level.

The regeneration of catalysts coated with carbonaceous deposits is generally effected by burning off the organic coatings with nitrogen-air mixtures (Chem. Eng. Sci. 46 (1991), 11–21). However, this method can be used only with catalysts which remain mechanically stable on reaction with air. Supported catalysts having a stable structure of oxidic material, such as $SiO_2$, $Al_2O_3$, $TiO_2$, can be successfully regenerated by this method. For instance, GB-A 2,284,163 describes the regeneration of a supported catalyst with Pt, Pd, Ru, Rh, Os, Ir or Ni by treatment with a gas containing at least chlorine and oxygen.

Catalysts with very high metal contents become damaged on burning off the organic deposits with air, altering their mechanical properties (see EP-A 61,042, for example).

It is known from the Journal of Catalysis 143 (1993), 187–200, that a nickel catalyst (25% by weight of Ni on $SiO_2$) which is used for the hydrogenation of acetonitrile in the gas phase can be regenerated by treatment with hydrogen at temperatures above 200° C.

The cited references do not reveal whether it is also possible to regenerate cobalt- and/or iron-containing catalysts under these conditions.

It is an object of the present invention to provide a process whereby it is possible to regenerate the cobalt- and iron-containing catalysts used in the hydrogenation of a compound containing at least one unsaturated carbon-nitrogen bond in a simple way, without incurring long shutdown times during the regeneration of the catalysts. More particularly, the object is to raise catalyst activity in respect of conversion and selectivity in the hydrogenation of the compound containing at least one unsaturated carbon-nitrogen bond as closely as possible back to the level of the unused catalyst.

We have found that these objects are achieved by a process for preparing an $NH_2$-containing compound by hydrogenating a compound containing at least one unsaturated carbon-nitrogen bond with hydrogen in the presence of a catalyst at temperatures not below room temperature and elevated hydrogen partial pressure in the presence or absence of a solvent, which comprises a) using a catalyst comprising a cobalt- and/or iron-containing catalyst, and b) after the conversion based on the compound to be hydrogenated and/or the selectivity based on the desired product has or have dropped below a defined value or the amount of an unwanted by-product has risen beyond a defined value, interrupting the hydrogenation by stopping the feed of the compound to be hydrogenated and of the solvent, if used, c) treating the catalyst at from 150 to 400° C. with hydrogen using a hydrogen pressure within the range from 0.1 to 30 MPa and a treatment time within the range from 2 to 48 h, and d) subsequently continuing the hydrogenation of the compound containing at least one unsaturated carbon-nitrogen bond.

We have also found a process wherein compounds containing at least one unsaturated carbon-nitrogen bond are hydrogenated in suspension or in a fixed-bed reactor in a downflow or upflow process; a process for preparing specifically 6-aminocapronitrile (ACN) and hexamethylenediamine (HMD); and also a process for regenerating cobalt- and iron-containing catalysts.

According to the invention, the starting compounds used are compounds containing at least one unsaturated carbon-nitrogen bond, such as a carbon-nitrogen double or triple bond. Preference is given to using a $C_4$–$C_8$-alkylnitrile or -dinitrile such as butanenitrile, pentanenitrile, hexanenitrile, heptanenitrile, octanenitrile, butanedinitrile (adiponitrile, short ADN), pentanedinitrile, hexanedinitrile, heptanedinitrile and octanedinitrile, especially adiponitrile, particularly preferably terminal $C_4$–$C_8$-dinitriles such as 1,4-dicyanobutane (adiponitrile), 1,5-dicyanopentane, 1,6-dicyanohexane, 1,7-dicyanoheptane and 1,8-dicyanooctane, especially adiponitrile, $C_5$–$C_8$-cycloalkylnitriles or -dinitriles such as cyclopentanecarbonitrile, cyclohexanecarbonitrile, cycloheptanecarbonitrile, cyclooctanecarbonitrile, cyclopentanedicarbonitrile, cyclohexanedicarbonitrile, and also aminonitriles containing from 4 to 8 carbon atoms, preferably α,ω-aminonitriles such as 5-aminovaleronitrile and 6-aminocapronitrile (ACN), especially ACN.

The nitriles, dinitriles and aminonitriles may also carry other functional groups as long as they do not impair the hydrogenation or their simultaneous or partial hydrogenation is desired. Examples are $C_1$–$C_4$-alkyl, aryl, especially phenyl, $C_5$–$C_8$-cycloalkyl, aminoalkyl, N-alkylaminoalkyl, N-(cyanomethyl)aminoalkyl and imino (C=NH, C=NR), preferably imino.

Particularly preferred compounds are ADN, ACN, 3-cyano-3,5,5-trimethylcyclohexylimine, NC—$(CH_2)_2$—N(H)—$(CH_2)_2$—CN, NC—$(CH_2)_2$—N(H)—$(CH_2)_2$—N(H)—$(CH_2)_2$—CN and 1-cyano-2-aminoethane.

The cobalt and/or iron catalysts can be used without support, especially for a fixed-bed or suspension process, for example in the form of Raney catalysts or in other customary unsupported forms, or as supported catalysts. The support used may typically be alumina, silica, activated carbons, titania and zirconia. In supported catalysts, the level of cobalt and/or iron relative to support is generally within the range from 3 to 95, preferably from 30 to 95, % by weight, depending on whether only one or both of cobalt and iron are present.

The catalysts can also be modified, if desired, with metals of group VIB (Cr, Mo, W), VIII of the periodic table of the elements (Ru, Os, Rh, Ir, Pd, Pt) and also copper, manganese and rhenium, in which case the cobalt and/or iron content of the catalyst is generally within the range from 50 to 99.9, preferably from 80 to 99, % by weight, based on the active components (cobalt and/or iron+modifier).

Furthermore, the catalysts may be modified with a compound based on an alkali metal or an alkaline earth metal such as lithium, sodium, potassium, rubidium, cesium, magnesium, calcium, strontium and barium, especially cesium. It is customary to use a weight ratio within the range from 0 to 5, preferably from 0.1 to 3, % by weight of alkali metal or alkaline earth metal, based on mass of cobalt and iron (one of which need not be present).

Preferred catalysts are unsupported iron and cobalt catalysts having an iron and/or cobalt content of at least 60% by weight, based on the mass of cobalt and/or iron and any modifier, if present.

Iron catalysts, which are chiefly used in ammonia synthesis, the Fischer-Tropsch reaction or as dehydrogenation catalyst for making styrene from ethylbenzene, may be prepared in various ways described in the literature. For instance, iron catalysts can be prepared from naturally occurring iron oxides such as hematite or magnetite or metallurgically produced (by oxidation) iron (see Ullmann's Encyclopedia of Industrial Chemistry, 5th Ed., Vol. A2, pages 169–172). Modifiers (also known as promoters) are customarily incorporated by conjoint melting of the oxides or applied to the inner surface by subsequent impregnation of the iron oxides. However, the iron oxide precursor may also be obtained by precipitation (see for example B. E. Leach, Applied Industrial Catalysis, 2 (1983), 177–180) or coprecipitation onto inert oxidic materials from aqueous iron salt solutions as carbonates or hydroxides. These precursors may be brought into a technically usable form in a conventional manner by tableting or extrusion (A. B. Stiles, Catalyst manufacture, New York 1983, pages 137–138, or M. Sittig, Catalyst Manufacture, Recovery and Use, 1972, Noyes data corporation, pages 217–221).

A further way of preparing iron catalysts is, for example, the thermal decomposition of iron cyanides to iron carbides and iron nitrides, which can generally be converted into alpha-iron by further heating (see Ullmann's Encyclopedia of Industrial Chemistry, 5th Ed., Vol. A2, pages 169–172).

Cobalt catalysts can be prepared by impregnating a ceramic support with aqueous or organic solutions of a cobalt-containing compound. The impregnation can be carried out on the ready-produced extrudate of the support or else on the support powder. If the ceramic support is used as powder, the cobalt-impregnated powder is customarily shaped, for example by extrusion or tableting, preferably after calcination.

If an impregnating step has failed to put sufficient cobalt on the support, for example because of the solubility of the cobalt salts used or the surface area of the support, it is possible, from observations to date, to repeat the impregnating until the desired amount of cobalt has been applied, in which case the resulting mass is dried and calcined after each impregnating step before the next impregnation is carried out.

It is also possible to prepare cobalt-containing catalysts by precipitation from aqueous or organic solution, in which case the modifiers (or promoters) are customarily coprecipitated or may be applied subsequently by impregnation. It is preferred to precipitate cobalt hydroxide or the corresponding carbonate or other sparingly soluble cobalt compounds. After precipitation, it is customary to dry the precipitate and then process the dried mass, for example by extrusion or tableting, although, if desired, it is possible to precede the shaping into extrudates or tablets with a calcination at temperatures within the range from 200 to 700° C. in order that certain, desirable solid-state phases may be obtained.

Before use as hydrogenation catalysts, the cobalt oxide and/or iron oxide precatalysts are advantageously reduced to the corresponding metals by means of a hydrogen treatment, in which case, in general, an oxide content of not more than 10% by weight, preferably of not more than 5% by weight, particularly preferably of not more than 1% by weight, based on the total mass of metal and oxide, is preferable from experience to date. This reduction of the oxide-containing materials to the corresponding active catalyst masses can be carried out under atmospheric or superatmospheric pressure at temperatures from 200° C. in a conventional manner.

The hydrogenations can be carried out in upflow, downflow or suspension.

When the reaction is carried out in a suspension, it is customary to choose temperatures within the range from 40 to 150° C., preferably within the range from 50 to 100° C., particularly preferably within the range from 60 to 90° C.; the pressure is generally chosen to be within the range from 2 to 20, preferably from 3 to 10, particularly preferably from 4 to 9, MPa. The residence times are essentially dependent on the desired yield, selectivity and the desired conversion; customarily, the residence time is selected so as to maximize the yield, for example within the range from 50 to 275, preferably within the range from 70 to 200, min.

In the suspension process, the solvent used is preferably ammonia, amines, diamines and triamines having from 1 to 6 carbon atoms such as trimethylamine, triethylamine, tripropylamine and tributylamine or alcohols, especially methanol and ethanol, particularly preferably ammonia. It is advantageous to use a concentration of the compound to be hydrogenated within the range from 10 to 90, preferably from 30 to 80, particularly preferably from 40 to 70, % by weight, based on the sum of compound to be hydrogenated and solvent.

The amount of catalyst used is generally within the range from 1 to 50, preferably from 5 to 20, % by weight, based on the amount of compound to be hydrogenated used.

The suspension hydrogenation can be carried out batchwise or, preferably, continuously, generally in the liquid phase.

The hydrogenation may also be carried out batchwise or continuously in a fixed-bed reactor in a downflow or upflow process, in which case it is customary to employ a temperature within the range from 30 to 200° C., preferably within the range from 50 to 150° C., and a pressure generally within the range from 2 to 30, preferably within the range from 3 to 20, MPa. The hydrogenation is preferably carried out in the presence of a solvent, preferably ammonia, amines, diamines and triamines having from 1 to 6 carbon atoms such as trimethylamine, triethylamine, tripropylamine and tributylamine or alcohol, preferably methanol and ethanol, particularly preferably ammonia. In a preferred embodiment, the amount of ammonia used is within the range from 0.5 to 10, preferably from 1 to 6, g per g of compound to be hydrogenated, especially adiponitrile. Preference is given to using a catalyst space velocity within the range from 0.1 to 2.0, preferably from 0.3 to 1.0, kg of the compound to be hydrogenated/l*h, especially adiponitrile/l*h. Here too it is possible to adjust the conversion and hence the selectivity in a specific manner by varying the residence time.

The hydrogenation can be carried out in a customary suitable reactor.

If the reaction is carried out in the gas phase, it is customary to use temperatures within the range from 100 to 250° C., preferably within the range from 160 to 200° C.; the pressure employed is generally within the range from 0.01 to 3, preferably from 0.09 to 0.5, MPa. Furthermore, the molar ratio of hydrogen to compound containing at least one unsaturated carbon-nitrogen bond is generally within the range from 2:1 to 300:1, preferably within the range from 10:1 to 200:1.

In a preferred embodiment, the hydrogenation of ADN is carried out in the presence of ammonia as solvent using fixed-bed catalysts by a process wherein, following the deactivation of the catalyst, ie. a decrease in the conversion of ADN and/or selectivity based on ACN below a defined value, first the feed of adiponitrile and ammonia is switched off, then the temperature is brought to 200–250° C., and subsequently the catalyst is treated for from ten to twenty hours with from 200 to 800, preferably from 500 to 700, especially 600, l of hydrogen/l of cat.xh. Thereafter the temperature is customarily brought back down to reaction temperature and the hydrogenation is continued.

Prior to starting the regeneration, it is preferable to remove the hydrogenation mixture still present in the reactor. It may be advantageous to wash the catalyst before the actual regeneration with the solvent present in the system, especially ammonia. The wash temperature employed is customarily within the range from 20 to 200° C., especially within the range from 20 to 100° C. It is generally advantageous to carry on the wash for a period of from 2 to 24 hours.

According to the invention, the regeneration of the catalyst is carried out at temperatures within the range from 150 to 400° C., preferably within the range from 180 to 350° C., especially within the range from 200 to 300° C., using a hydrogen pressure within the range from 0.1 to 30 MPa, preferably within the range from 0.1 to 20 MPa. A continuous process is customarily carried out with the hydrogen rate within the range from 100 to 1500, preferably within the range from 200 to 1000, l of hydrogen/l of reactor volumex hour.

The process of the invention makes it possible to achieve distinct improvements in the life and space-time yield of cobalt- and/or iron-containing catalysts in the hydrogenation of compounds containing at least one unsaturated carbonnitrogen bond, especially in the hydrogenation of adiponitrile to aminocapronitrile and hexamethylenediamine (nylon 6 and nylon 66 intermediates).

EXAMPLES

Example 1

Preparation of an Unsupported Cobalt Catalyst

20% strength by weight sodium carbonate solution was added a little at a time to an aqueous solution of cobalt nitrate, manganese nitrate and phosphoric acid in water containing 10% by weight of cobalt (calculated on the basis of cobalt nitrate), 0.55% by weight of manganese (calculated from the amount of manganese nitrate) and 0.45% by weight of $H_3PO_4$ at 50° C. in such a way as to always produce a pH of 6 on completion of the addition of the sodium carbonate solution; the corresponding carbonates were precipitated. On completion of the precipitation, discernible from the fact that the established pH of 6 did not change, further sodium carbonate solution was added until a pH of 7.5 was obtained. The resulting precipitate was washed nitrate and sodiumfree by washing the precipitate with water until a final conductivity of 20 μsiemens was obtained and, according to Merckoquant® test strips for nitrate (from Merck), the nitrate content of the solution was less than 0.02% by weight. The precipitate thus washed was suspended in water and sprayed into a spray-tower (inlet temperature=550° C.). The sprayed material was dried at 500° C., mulled and shaped in an extruder into extrudates 4 mm in diameter and 1 cm in length. The extrudates were dried at from 100 to 120° C., and calcined at 900° C. for 1 h. The calcined product had a composition of 90% by weight of CoO, 5% by weight of $Mn_2O_3$, 3% by weight of $P_2O_5$ and 2% by weight of $Na_2O$. The extrudates thus obtained were reduced at 320° C. in a stream of hydrogen for 16 h and passivated at room temperature with a nitrogen-air mixture (5% by volume of air, 95% by volume of nitrogen).

Example 2

Preparation of an Unsupported Iron Catalyst

The method described in Catalyst Manufacture, A. B. Stiles, T. A. Koch (1995), pages 167/68, was followed to melt a mixture of iron oxide (magnetite) with the promoters $Al_2O_3$, $K_2CO_3$ and calcium carbonate at from 1600 to 2000° C. The melt was subsequently cooled and comminuted. The material obtained (catalyst in the oxidic state) had the following composition: 1.1% by weight of $K_2O$, 3.0% by weight of $Al_2O_3$, 2.3% by weight of CaO, remainder FeO and $Fe_2O_3$. To obtain a usable catalyst, the material obtained was treated at 450° C. with hydrogen at 3 MPa for 32 h and then passivated at room temperature with a nitrogen/air mixture (5% by volume of air, 95% by volume of nitrogen). The ratio of mass of metals to mass of oxides ("degree of reduction") was 9:1.

Example 3

Fixed-Bed Hydrogenation in the Liquid Phase

A tubular reactor 2 m in length and 2.5 cm in internal diameter was packed with 750 ml (1534 g) of the passivated catalyst of Example 1. The passivated catalyst was then activated over 48 h in a stream of nitrogen (500 l/h) under atmospheric pressure by raising the temperature from 30° C. to 280° C. (during which time previously unconverted CoO was reduced to Co).

After lowering the reactor inlet temperature to 45° C. and the reactor outlet temperature to 85° C., the reactor was supplied under a total pressure of 20 MPa with a mixture of 400 ml/h of adiponitrile, 600 ml/h of ammonia and 500 l/h of hydrogen. In addition, to remove the heat, about four times the feed quantity (4.2 l/h) was recycled via a heat exchanger. Under these conditions, the adiponitrile conversion was 70%. The initial reaction mixture contained 30% by weight of ADN, 35% by weight of ACN and 34.5% of HMD (ACN selectivity: 50%, ACN+HMD selectivity:

>99%). Following a run of 3,600 h, the ACN selectivity dropped from an initial 50% to 23% while the conversion remained unchanged.

Thereafter the dinitrile and ammonia feed was switched off and the catalyst regenerated in the reactor over 12 hours at 200° C. and a total pressure of 200 bar (at 500 l/h of hydrogen). A renewed startup under identical conditions (see above) produced an increase in the selectivity to 50%; that is, the catalyst had been restored to its initial selectivity.

Example 4

Fixed-Bed Hydrogenation in the Liquid Phase

A tubular reactor 2 m in length and 2.5 cm in internal diameter was packed with 800 ml (1598 g) of the passivated catalyst of Example 1. The catalyst was then activated over 48 h under atmospheric pressure in a stream of hydrogen (500 l/h) by raising the temperature from 30° C. to 320° C. (in which period residual CoO was reduced to Co).

After lowering the reactor inlet temperature to 120° C. and the reactor outlet temperature to 140° C., the reactor was supplied at 25 MPa in the downflow direction with a mixture of 180 ml/h of 3-cyano-3,5,5-trimethylcyclohexylimine, 1700 ml/h of ammonia and 500 ml/h of hydrogen. Under these conditions the imine conversion was 100%. The yield of 3-aminomethyl-3,5,5-trimethylcyclohexylamine was 94% (selectivity: 94%). 3-Cyano-3,5,5-trimethylcyclohexylamine was a hydrogenation intermediate and hence an indicator of the catalyst activity. The concentration of this compound rose from an initial 0 ppm to 1500 ppm (based on the reaction mixture) after 5700 h, so that catalyst regeneration appeared to be necessary for product specification reasons.

Thereafter the nitrile and ammonia feed was switched off and the catalyst regenerated in the reactor over 24 h at 300° C. and a total pressure of 25 MPa (at 500 l/h of hydrogen). A renewed startup under identical conditions as above produced a drop in the intermediate concentration to 200 ppm; that is, the catalyst had been almost completely restored to its initial activity.

Example 5

Fixed-Bed Hydrogenation in the Liquid Phase

A tubular reactor 7 m in length and 10.5 cm in internal diameter was packed with 60 l (130 kg) of the catalyst obtained in Example 2 (degree of reduction 9:1) and then the catalyst was activated over 72 h at 370° C. and a total pressure of 15 MPa (reducing the remaining iron oxide to iron) by first passing nitrogen through the reactor and then replacing the nitrogen step by step with hydrogen during the first 24 h.

After lowering the reactor inlet temperature to 110° C. and the reactor outlet temperature to 135° C., the reactor was supplied under a total pressure of 25 MPa with a mixture of 30 kg/h of ADN, 50 l/h of liquid ammonia and 40 standard m³/h of hydrogen. In addition, to remove the heat, five times the feed quantity (400 l/h) was recirculated via a heat exchanger (giving a recycle stream temperature at the reactor inlet of 110° C.). Under these conditions the ADN conversion was 70%. The initial reaction mixture contained 30% by weight of ADN, 35% by weight of ACN and 34.5% by weight of HMD (ACN selectivity: 50%, ACN+HMD selectivity: >99%). After 800 h the catalyst was specifically deactivated by switching off the feeds without rinsing.

For regeneration, the catalyst was treated in the reactor initially with nitrogen (80 m³/h) at a temperature within the range from 200 to 250° C. and a pressure of 15 MPa, for 24 h. This was followed by heating to 270° C. and stepwise replacement of the nitrogen (80 m³/h) with hydrogen over 5 h. During the replacement of nitrogen with hydrogen the temperature was likewise increased stepwise to 380° C. Finally the reactor was maintained at a temperature within the range from 350 to 380° C. and a hydrogen pressure of 20 MPa for 24 h. On a renewed startup under the same conditions as indicated above the selectivity of the catalyst was back to its initial level.

We claim:

1. A process for preparing an $NH_2$-containing compound by hydrogenating a compound having at least one unsaturated carbon-nitrogen bond with hydrogen in the presence of a catalyst at an elevated hydrogen partial pressure in the presence or absence of a solvent, which comprises
   a) using a catalyst comprising a cobalt- and/or iron catalyst, and
   b) interrupting the hydrogenation by stopping the feed of the compound to be hydrogenated,
   c) treating the catalyst at from 150 to 400° C. with hydrogen using a hydrogen pressure within the range from 0.1 to 30 MPa and a treatment time within the range from 2 to 48 h, and
   d) subsequently continuing the hydrogenation of the compound having at least one unsaturated carbon-nitrogen bond.

2. The process of claim 1, wherein the compound having at least one unsaturated carbon-nitrogen bond is a $C_4$–$C_8$-alkylnitrile, a $C_5$–$C_8$-cycloalkylnitrile, a $C_4$–$C_8$-alkyldinitrile or a $C_5$–$C_8$-cycloalkyldinitrile.

3. The process of claim 1, wherein the compound having at least one unsaturated carbon-nitrogen bond is adiponitrile and 6-aminocapronitrile and hexamethylenediamine are obtained in the process.

4. The process of claim 1, wherein the hydrogenation of the compound having at least one unsaturated carbon-nitrogen bond is carried out in suspension at a temperature within the range from 40 to 150° C. and at a pressure within the range from 2 to 20 MPa.

5. The process of claim 1, wherein the hydrogenation of the compound having at least one unsaturated carbon-nitrogen bond is carried out in a fixed-bed reactor in a downflow or upflow process at a temperature within the range from 30 to 200°C. and at a pressure within the range from 2 to 30 MPa.

6. A process for regenerating a cobalt- and/or iron catalyst, which comprises treating the catalyst with hydrogen at from 150 to 400° C. using a hydrogen pressure within the range from 0.1 to 30 MPa and a treatment time within the range from 2 to 48 h.

7. The process of claim 3, wherein the hydrogenation of adiponitrile is carried out in suspension at a temperature within the range of from 40 to 150° C. and at a pressure within the range of 2 to 20 MPa.

8. The process of claim 3, wherein the hydrogenation of adiponitrile is carried out in a fixed-bed reactor in a downflow or upflow process at a temperture within the range from 30 to 200° C. and at a pressure within the range from 3 to 30 MPa.

* * * * *